United States Patent
Niethammer

(10) Patent No.: US 7,715,603 B2
(45) Date of Patent: May 11, 2010

(54) METHOD FOR PROCESSING AVAILABLE TIME/PHASE-DEPENDENT PRIMARY DATA SETS OF A COMPUTER TOMOGRAPH OF A DISPLACED OBJECT TO FORM A THREE-DIMENSIONAL IMAGE SEQUENCE

(75) Inventor: Matthias Niethammer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1119 days.

(21) Appl. No.: 10/546,998

(22) PCT Filed: Jan. 30, 2004

(86) PCT No.: PCT/EP2004/000895

§ 371 (c)(1),
(2), (4) Date: Aug. 26, 2005

(87) PCT Pub. No.: WO2004/077361

PCT Pub. Date: Sep. 10, 2004

(65) Prior Publication Data

US 2006/0188067 A1     Aug. 24, 2006

(30) Foreign Application Priority Data

Feb. 27, 2003   (DE) ................. 103 08 641

(51) Int. Cl.
*G06K 9/00* (2006.01)
(52) U.S. Cl. .................................... 382/128
(58) Field of Classification Search ................ 382/128, 382/131, 132; 600/428; 378/4, 901
See application file for complete search history.

(56) References Cited

U.S. PATENT DOCUMENTS

| | | | |
|---|---|---|---|
| 5,832,051 A | 11/1998 | Lutz | |
| 6,266,553 B1 * | 7/2001 | Fluhrer et al. | ................ 600/428 |
| 6,381,296 B1 * | 4/2002 | Nishiura | ......................... 378/4 |

(Continued)

FOREIGN PATENT DOCUMENTS

DE    197 40 214 A1    4/1999

(Continued)

OTHER PUBLICATIONS

Heinz Morneburg, Bildgebende Systeme für die medizinische Diagnostik, Publicis MCD Verlag, 3., wesentlich überarbeitete und erweiterte Auflage, 1995.

(Continued)

*Primary Examiner*—Charles Kim
*Assistant Examiner*—Claire Wang
(74) *Attorney, Agent, or Firm*—Harness, Dickey & Pierce, P.L.C.

(57) ABSTRACT

A method and a device are disclosed for processing available time/phase-dependent primary data sets of a computer tomography of a displaced object, preferably a beating heart, in order to produce an image sequence 3D-recording set records for representing the displacement of an object. The method includes the following steps: calculating and representing of a 3D reference display of any particular orientation in relation to any particular displacement phase of an available present primary data sequence of a CT-scan, determining the desired calculation parameters of the image sequence which is to be calculated, single transfer of the calculation parameter to the calculation process and automatic creation of the entire image sequence with the predetermined calculation parameters.

20 Claims, 2 Drawing Sheets

U.S. PATENT DOCUMENTS

| | | |
|---|---|---|
| 6,504,893 B1 | 1/2003 | Flohr |
| 6,556,697 B1 | 4/2003 | Bruder et al. |
| 6,560,309 B1 | 5/2003 | Becker et al. |

FOREIGN PATENT DOCUMENTS

| | | |
|---|---|---|
| DE | 196 22 075 C2 | 10/1999 |
| DE | 198 42-240 A1 | 3/2000 |
| DE | 198 42 238 A1 | 4/2000 |
| DE | 199 57 083 A1 | 6/2001 |
| DE | 199 57 082 A1 | 8/2001 |
| EP | 1 061 474 A1 | 6/1999 |
| WO | WO 99/00675 | 1/1999 |
| WO | WO 02/43007 A1 | 5/2002 |

OTHER PUBLICATIONS

Willi A. Kalender, Computertomographie, Publicis MCD Verlag, 2000, ISBN 3-89578-082-0.

Joseph M. Reinhard, Cue-Based Segmentation of 4D Cardiac Image Sequences, Computer Vision and Image Understanding 77, 251-262 (2000).

Javier Olivan, Jaap Smit and Kees Slump, University of Twente, Interactive 4-D Cardiac MRI Imaging Based on Iso-Surface Volume Rendering, Medical Imaging 2002: Visualization, Image-Guided Procedures, and Display, Seong K. Mun, Editor, Proceedings of SPIE vol. 4681 (2002).

G. Alan Johnson, Gated Multiplanar Cardiac Computer Tomography, Technical Developments and Instrumentation.

Marc Kachelriess, ECG-Correlated Imaging of the Heart with Subsecond Multislice Spiral CT, IEEE Transactions on Medical Imaging, vol. 19, No. 9, Sep. 2000.

Marc Kachelriess, Kymogram detection and kymogram-correlated image reconstruction from subsecond spiral computed tomography scans of the heart, Medical Physics, vol. 29, No. 7, Jul. 2002.

International Search Report.
International Preliminary Examination Report.
German Office Action.
German Translation Aid.

* cited by examiner

METHOD FOR PROCESSING AVAILABLE TIME/PHASE-DEPENDENT PRIMARY DATA SETS OF A COMPUTER TOMOGRAPH OF A DISPLACED OBJECT TO FORM A THREE-DIMENSIONAL IMAGE SEQUENCE

This application is the national phase under 35 U.S.C. §371 of PCT International Application No. PCT/EP2004/000895 which has an International filing date of Jan. 30, 2004, which designated the United States of America and which claims priority on German Patent Application number DE 103 08 641.2 filed Feb. 27, 2003, the entire contents of which are hereby incorporated herein by reference.

FIELD

The invention generally relates to a method for processing available time-dependent/phase-dependent primary data sets of a computed tomograph of a moving object, preferably a beating heart, in order to produce an image sequence of 3D image sets for representing the object movement.

BACKGROUND

The technology of computed tomography units is generally known. Reference may be made in this context to two papers entitled "Bildgebende Systeme für medizinische Diagnostik" ["Imaging systems for medical diagnostics"], ISBN 3-89578-002-0, in particular Chapters 5 and 9, and to "Computertomographie" ["Computed tomography"], ISBN 3-89578-082-0, in particular Chapter 3, preferably to Chapter 3.4.

Cardiac computed tomography units that are suitable for the three-dimensional display of the periodic heart movement are likewise described in patent literature. Reference may be made by way of example to the applicant's laid-open patent applications DE 199 57 082 A1, DE 199 57 083 A1, DE 198 42 238 A1, DE 198 42 240 A1, DE 197 40 214 A1 and DE 196 22 075 A1.

The use of such cardiac CT units renders it possible to represent the movement of the heart by making three-dimensional recordings of the heart over the entire course of the movement. That is to say, it is therefore possible to produce an image sequence that displays the movement of the heart three-dimensionally in the manner of a film by juxtaposing a multiplicity of temporally offset 3D image sets.

When viewing such a series diagnostically, the problem arises that the images recorded by the computed tomograph are basically at first available in views which correspond to the patient's longitudinal axis, since this corresponds to the normal infeed direction of the patient couch when making CT recordings. However, it is advantageous for the diagnostic assessment to view a display of the heart in specific preferred directions such as, for example, the "long heart axis", the "short heart axis" or a recording axis that corresponds to the so called "4-chamber view or 5-chamber view".

With the units currently on the market, these recording sequences are produced in the desired viewing mode by respectively producing the individual 3-dimensional recordings of the desired image sequence individually from the primary data of the CT and reproducing them on a monitor, the operator subsequently having to input the desired image parameters such as slice thickness, axis orientation etc. These inputs are used to calculate and store the desired view from the available 3D display in z-direction.

During the conversion process of the image sequence into the desired view, this procedure repeatedly requires the desired recording parameters to be input manually. Thus, in this case the process of reconstructing a 3D recording set of a specific cardiac phase by inputting the desired image parameters, converting the view in accordance with the desired image parameters and subsequently storing this changed 3D recording set is repeated until all the individual phases of the heart have been represented such that an entire image sequence composed of a multiplicity of 3D recording sets with the desired image parameters is subsequently present.

Such a method is complicated and affected by error. Furthermore, this entails a high arithmetic capability that is not mandatory.

SUMMARY

It is an object of at least one embodiment of the invention to make available a simplified method for processing available time-dependent/phase-dependent primary data sets of a computed tomograph of a moving object which is distinguished by a simple mode of operation with improved utilization of the arithmetic capability.

The inventor has found, in at least one embodiment, that a substantial easing of the work load is possible when compiling 3D image sequence by using a single reconstructed 3D recording for a one-off determination of the image parameters from which the image sequence is to be produced, such that the desired orientation of the 3D view to be compiled feature in the parameters that determine the reconstruction of the finished three-dimensional image. Thus the entire image sequence are compiled by a single input with the aid of a multiplicity of 3D recording sets relating to respective different instants. This can also be performed directly from the available primary data set of the CT scan of the moving object, in particular a moving heart, or by the automatic reorientation of 3D recording sets already reconstructed.

In accordance with this finding, the inventor proposes a method, in at least one embodiment, for processing available time-dependent/phase-dependent primary data sets of a computed tomograph of a moving object, preferably a beating heart, to produce an image sequence of 3D recording sets for representing the object movement, the method having the following method steps:

calculating and representing a three-dimensional reference display of any particular orientation in relation to any particular movement phase from an existing primary data set of a CT scan, determining the desired calculation parameters $R_i$ of the image sequence to be calculated, one-off transfer of the calculation parameters $R_i$ to the calculation process, and automatically compiling the entire image sequence with the aid of the specified calculation parameters $R_i$ by reconstruction from the primary data sets of the detector.

It is possible thereby to calculate the image sequence from 3D recording sets previously compiled in any particular recording direction for all time intervals or recording instants $t_x$, these subsequently being transformed automatically into the desired recording direction.

However, it is also the fundamentally preferred possibility of reconstructing the image sequence directly from the primary data set with the aid of the input calculation parameters, as a result of which additional arithmetic capability can be saved.

According to the invention, in at least one embodiment, the desired calculation parameters $R_i$ include the desired recording axis A relative to the reference display, the desired time interval/phase interval $\Delta t$ of the image sequence to be calculated, and the recording periods or the number of the 3D recording sets that are to be calculated.

Depending on the display quality desired, it can also be provided to specify a desired slice thickness d for the image sequence to be calculated in the calculation parameters.

The inventor also proposes, in at least one embodiment, with reference to the definition of the orientation of the recording axis A that this be undertaken by visually controlled and manual insertion of an axis in a three-dimensional reference display on a monitor.

Alternatively, however, there is also the possibility of defining the orientation of the recording axis A by means of an image recognition method for the object viewed and an automatic assignment to prescribed standard axes.

It is thereby possible for the compilation of the desired image sequences in relation to prescribed standard axes to be further automated.

With reference to the image recognition method in at least one embodiment, it is possible to make use of techniques known per se, in particular neuron networks, which recognize characteristic zones of the heart such as, for example, the apex of the heart, blood vessel entry points, etc., and automatically determine in accordance with these characteristic zones the standard axes which then correspond to the known views of "the long heart axis", "the short heart axis" or the "4-chamber view or 5-chamber view".

The inventor also proposes that at least two two-dimensional displays along different, preferably mutually perpendicular recording axes are used as three-dimensional reference display. This type of display renders it possible to determine the three-dimensional orientation of the desired recording axis by means of two-dimensional inputs. However, it is also possible as an alternative to display the heart directly in spatial terms, for example by using so called 3D spectacles.

In accordance with the basic idea of the method according to the invention in at least one embodiment, the inventor also proposes an evaluation unit for compiling image sequences of the moving examination object for a computed tomography unit for scanning a moving examination object, preferably for a cardiac CT unit, which includes a device/system for carrying out the above described method in at least one embodiment, this device/system preferably being implemented by programs or program modules.

BRIEF DESCRIPTION OF THE DRAWINGS

The invention is described in more detail below with reference to the example embodiment with the aid of the figures, in which, in detail.

DETAILED DESCRIPTION OF THE EXAMPLE EMBODIMENTS

Figure 1:
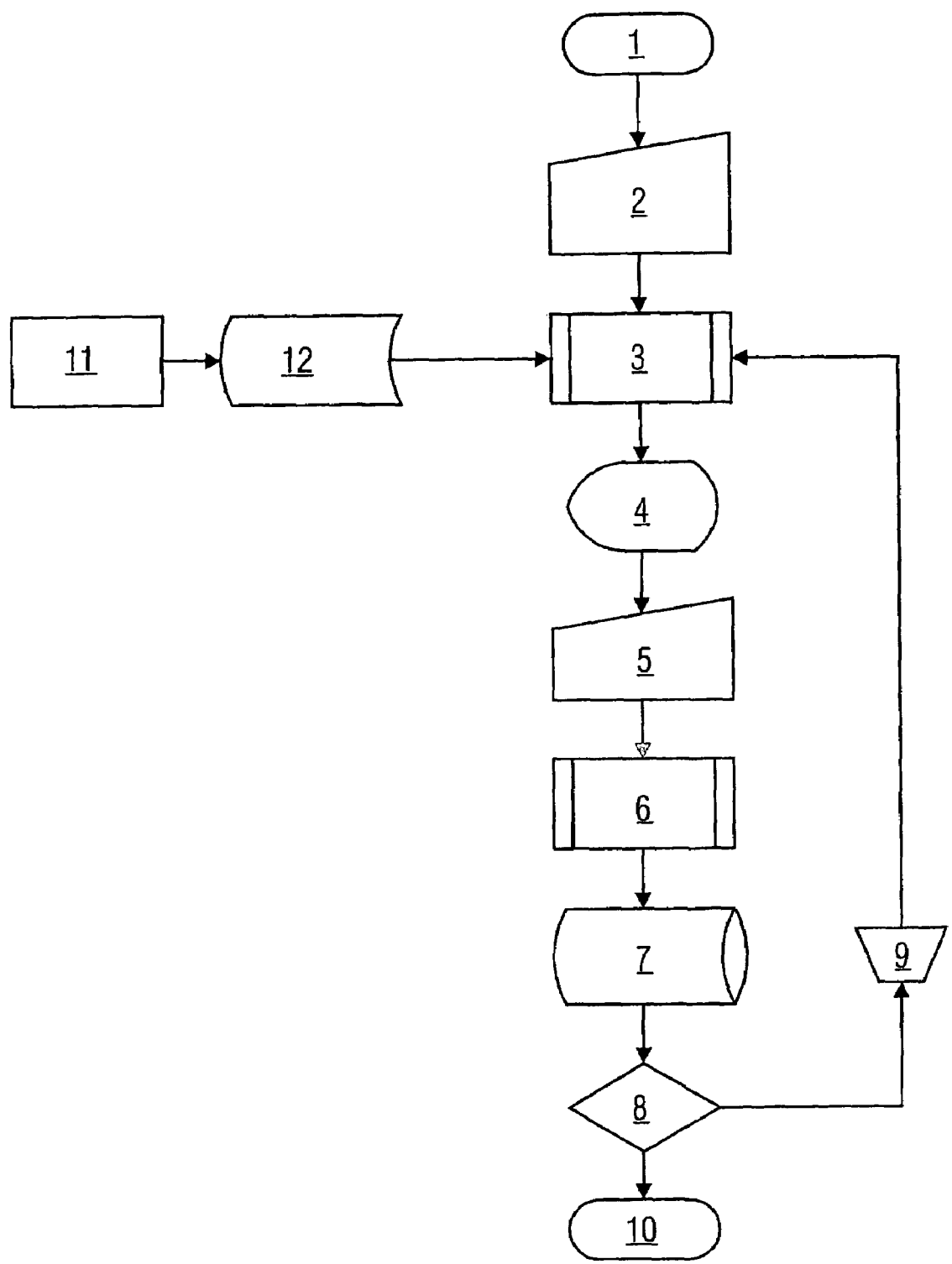
FIG. 1 shows a flowchart for processing available primary data sets to form a three-dimensional series in accordance with the prior art.

FIG. 1 shows the currently known method for processing available phase-dependent primary data sets of a computed tomograph of a beating heart for producing an image sequence of 3D recording sets in order to display the movement of the heart.

As shown at left, the first step is to carry out a CT scan 11 of a patient, the data obtained from the CT scan being stored as primary data set 12 and then being available for further processing.

The actual method for processing the three-dimensional image sequence begins at the starting point 1. Here, an operator manually determines a selection of a 3D display by inputting the desired instant $t_x$ and the volume to be calculated in accordance with method step 2. Subsequently, the reconstruction 3 of the selected 3D image data set is performed, and output on a monitor in method step 4.

In method step 5, the operator now has to use the 3D display present for him to select the parameters with the aid of which the available 3D image data set is converted in order to be transferred into the desired recording axis. In essence, this means specifying the orientation of the recording axis in relation to the axis used in the reference recording, which is generally identical to the z-axis of the recording tomography system.

Once the operator has selected the parameters, these selected parameters are transferred to the computer, which uses these new parameters to carry out a transformation of the already calculated 3D image data set with reference to the new selected recording axis and, if appropriate, further changed image parameters in method step 6. This newly obtained 3D image data set for a specific instant or a specific heart phase is now stored in method step 7. This can be performed either by a manual input or else automatically. Subsequently, the decision is taken at the decision point 8 as to whether a further 3D image data set relating to another instant or another heart phase is to be processed, or whether the image sequence is finished.

If the operator's manual input 9 defines the situation as "not finished", there is a jump back to method step 3 such that reconstructions of 3D image data sets take place, and a corresponding transformation onto the desired recording axis takes place until the entire image sequence is transformed and the loop is interrupted at the decision point 8.

If the operator's input 9 defines the situation as "finished", the end 10 of the method is initiated.

This mode of procedure indicates that the operator is tied to the computer during the entire processing operation, since manual inputs are always being required again as the loop runs between method steps 3 and 8.

Figure 2:
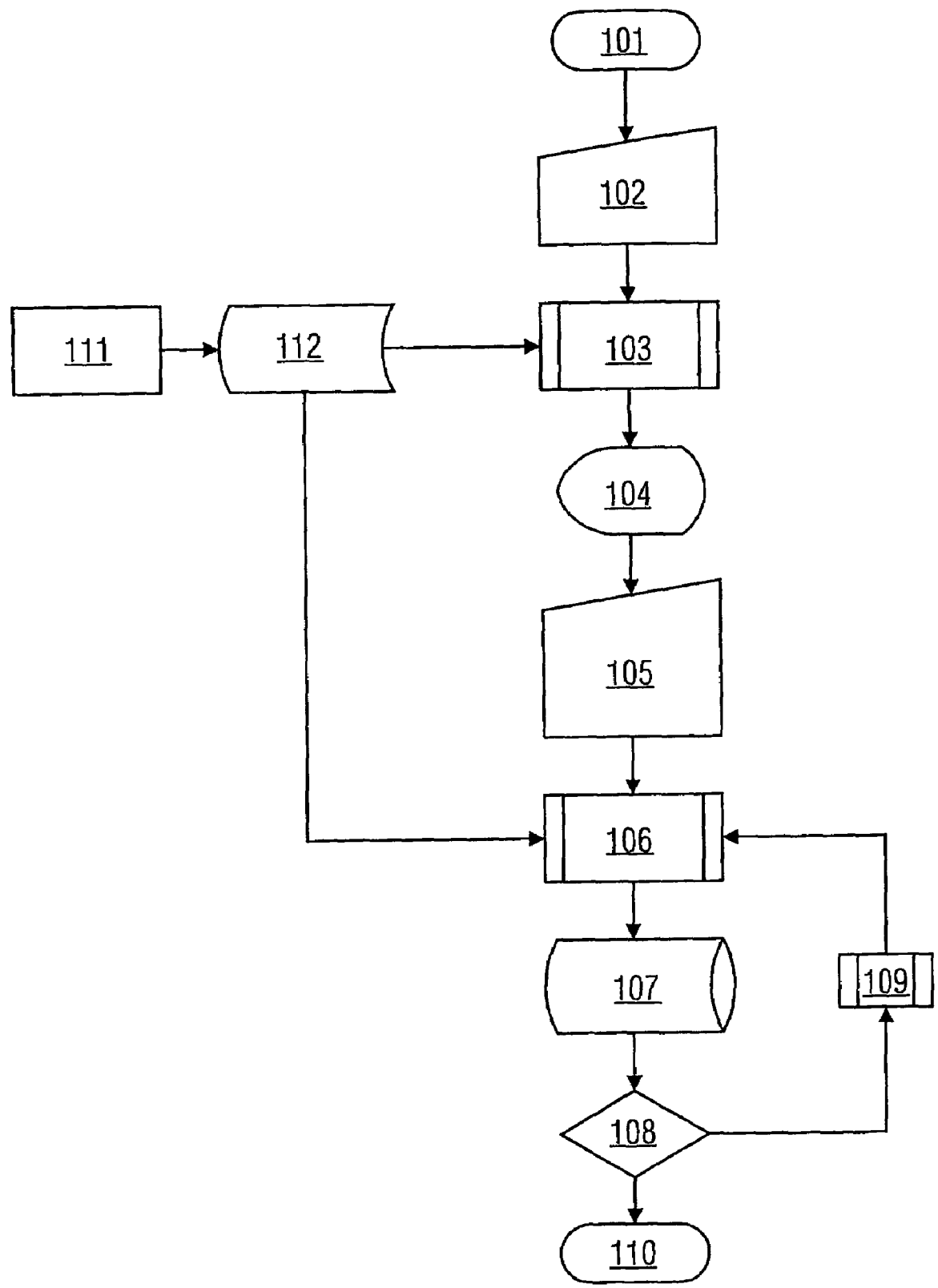
FIG. 2 shows a flowchart of the inventive method for processing available primary detail sets of a CT in order to produce an image sequence.

The method according to at least one embodiment of the invention avoids this ever recurring manual input from the operator by virtue of the fact that the desired parameters of the image sequence are defined by a one-off manipulation, after which the computer can automatically process the production of the desired 3D image data sets of the entire image sequence. An example execution of at least one embodiment of such a method is illustrated in FIG. 2, the special method with direct calculation of the desired view of the image sequence from the primary data being shown here.

Just as is known from the prior art, a CT scan 111 of a patient with a beating heart is used to compile and store a primary data set 112 that is available for the further processing of the actual image display.

The actual compilation of the image sequence again begins with the starting point 101. Then, the 3D display at any particular instant is selected in method step 102 by manual input. The computer subsequently carries out in method step 103 a reconstruction of the desired 3D image data set, doing so with the aid of the primary data set 112, and, in method step 104, outputs the 3D illustration of the heart thus obtained on a monitor, as a three-dimensional display.

There is subsequently again a need for a manual input in which the operator determines in method step 105 the parameters for the image sequence to be calculated, the result being, in particular, to determine the recording axis a, the slice thickness d and the time interval Δt of the image sequence to be compiled.

If these data are input at an input unit of the computer, there is subsequently no longer any need for manual activity by the operator. The subsequent reconstruction of a 3D image data set, the storage of the 3D image data set obtained, and the decision as to whether the loop must be carried out again with an altered time parameter can now be carried out automatically in the computer such that the loop of at least one embodiment of method points 106 to 108 is possible without manual intervention by the operator.

Here, the reconstruction of a 3D image data set is carried out in method step 106, the storage of the 3D image data set is carried out in method step 107, and the decision as to whether all the 3D image data sets are finished is carried out in method step 108 by the automatic input in method step 109. If the decision is made automatically in method step 108 that all the 3D image data sets are finished, this leads to the end 110 of the method. If all 3D image data sets that are required for the image sequence have been calculated, the loop is terminated, and the image sequence is available in the way desired.

By analogy with the method of at least one embodiment illustrated in FIG. 2, it is also possible in the automated loop firstly to calculate the image sequence with the aid of all the 3D image sets from the primary data sets, and to use these 3D image data sets to transform the desired recording direction for the entire image sequence.

At least one embodiment of this method requires a substantially lesser imposition on the operator's time, thus leading to savings in costs. Furthermore, there is less of a claim on the arithmetic capability because of the more rational type of calculation of the image sequence.

It goes without saying that the above-named features of at least one embodiment of the invention can be used not only in the respectively specified combination, but also in other combinations or on their own without departing from the scope of the invention.

In the case of the method according to at least one embodiment of the invention, the transformation to a desired image plane takes place, for example, by way of multiplanar reformatting (MPR), which is known per se.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for processing at least one of time and phase dependent primary data sets of a computed tomograph of a moving object, the method comprising:
    calculating and representing a three-dimensional reference display of any particular orientation in relation to any particular movement phase from an existing primary data set of a CT scan using desired calculation parameters;
    determining the desired calculation parameters of an image sequence to be calculated, the desired calculation parameters being associated with an orientation, a slice thickness and a display interval of an image of the image sequence and the image sequence being a plurality of images associated with the CT scan;
    transferring and using the desired calculation parameters to the calculating step one time via one time input of a user; and
    automatically compiling the image sequence with the one time transferred desired calculation parameters by reconstruction from primary data sets of a detector.

2. The method as claimed in claim 1, wherein at least one calculation parameter represents a desired recording axis relative to the reference display.

3. The method as claimed in claim 1, wherein at least one calculation parameter represents a desired at least one of time and phase interval of the image sequence to be calculated.

4. The method as claimed in claim 1, wherein at least one calculation parameter represents a desired recording period.

5. The method as claimed in claim 4, wherein the recording period is determined by a number of the 3D recording sets and a time interval.

6. The method as claimed in claim 1, wherein at least one calculation parameter represents a desired slice thickness of the image sequence to be calculated.

7. The method as claimed in claim 1, wherein a definition of the orientation of a recording axis is undertaken by visually controlled and manual insertion of an axis in the three-dimensional reference display on a monitor.

8. The method as claimed in claim 1, wherein a definition of the orientation of a recording axis is automatically performed by image recognition methods for the moving object viewed and assignment to prescribed standard axes.

9. The method as claimed in claim 8, wherein at least one of standard views of "long heart axis", "short heart axis", "4-chamber view" and "5-chamber view" is automatically proposed.

10. The method as claimed in claim 1, wherein at least two two-dimensional displays along different perpendicular recording axes are used as the three-dimensional reference display.

11. The method as claimed in claim 1, wherein a spatial display is used as the three-dimensional reference display.

12. An evaluation unit for compiling image sequences of a moving examination object for a computed tomography unit scanning a moving examination object, wherein at least one of programs and program modules are included in a computer readable medium for implementing the method of claim 1.

13. An evaluation unit for compiling image sequences of a moving examination object for a computed tomography unit scanning a moving examination object, wherein at least one of programs and program modules are included in a computer readable medium for implementing the method of claim 2.

14. The method as claimed in claim 2, wherein at least one calculation parameter represents a desired at least one of time and phase interval of the image sequence to be calculated.

15. The method as claimed in claim 2, wherein the at least one calculation parameter represents a desired recording period.

16. The method as claimed in claim 3, wherein the at least one calculation parameter represents a desired recording period.

17. The method as claimed in claim 2, wherein the at least one calculation parameter represents a desired slice thickness of the image sequence to be calculated.

18. The method as claimed in claim 2, wherein a definition of the orientation of a recording axis is automatically performed by image recognition methods for the moving object viewed and assignment to prescribed standard axes.

19. The method as claimed in claim 18, wherein at least one of the standard views of "long heart axis", "short heart axis", "4-chamber view" and "5-chamber view" is automatically proposed.

20. An apparatus, comprising:
means for calculating and representing a three-dimensional reference display of any particular orientation in relation to any particular movement phase from an existing primary data set of a CT scan using desired calculation parameters;
means for determining the desired calculation parameters of the image sequence to be calculated, the desired calculation parameters being associated with an orientation, a slice thickness and a display interval of an image of the image sequence and the image sequence being a plurality of images associated with the CT scan;
means for transferring and using the desired calculation parameters to the calculating step one time via one time input of a user; and
means for automatically compiling an entire image sequence with the one time transferred desired calculation parameters by reconstruction from primary data sets of a detector.

* * * * *